United States Patent [19]

Schröder et al.

[11] Patent Number: 5,000,751
[45] Date of Patent: Mar. 19, 1991

[54] APPARATUS FOR LASER SURGERY AND PARTICULARLY FOR THE KERATOTOMY OF THE CORNEA (III)

[75] Inventors: Eckhard Schröder, Eckental; Reinhardt Thyzel, Heroldsberg, both of Fed. Rep. of Germany

[73] Assignee: Aesculap AG, Tuttlingen, Fed. Rep. of Germany

[21] Appl. No.: 398,313

[22] Filed: Sep. 13, 1989

Related U.S. Application Data

[63] Continuation of Ser. No. 213,460, Jun. 29, 1988, abandoned, which is a continuation of Ser. No. 30,830, filed as PCT DE86/00268 on Jun. 30, 1986, published as WO87/00038 on Jan. 15, 1987, abandoned.

[51] Int. Cl.⁵ .............................................. A61N 5/06
[52] U.S. Cl. .................................... 606/4; 606/5; 128/395
[58] Field of Search ................... 351/205, 214, 221; 128/303.1, 395, 397, 398; 606/3-5

[56] References Cited

U.S. PATENT DOCUMENTS

| | | | |
|---|---|---|---|
| 3,348,547 | 10/1967 | Kavanagh | 128/395 |
| 3,621,181 | 11/1971 | Young | 128/395 |
| 3,720,213 | 3/1973 | Hobart et al. | 128/395 |
| 3,804,095 | 4/1974 | Bredemeier | 128/303.1 |
| 4,091,814 | 5/1978 | Togo | 128/303.1 |
| 4,164,222 | 8/1979 | Prokhorov et al. | 128/303.1 |
| 4,266,862 | 5/1981 | Trötscher et al. | 351/211 |
| 4,309,998 | 1/1982 | Aron Nee Rosa et al. | 128/395 |
| 4,461,294 | 7/1984 | Baron | 128/395 |
| 4,499,897 | 2/1985 | Roussel | 128/395 |
| 4,538,608 | 9/1985 | L'Esperance, Jr. | 606/3 |
| 4,554,917 | 11/1985 | Tagnon | 128/303.1 |
| 4,565,197 | 1/1986 | Daly | 128/303.1 |
| 4,638,801 | 1/1987 | Daly et al. | 128/303.1 |
| 4,648,400 | 3/1987 | Schneider et al. | 128/303.1 |

Primary Examiner—Lee S. Cohen
Assistant Examiner—David Shay
Attorney, Agent, or Firm—Barnes & Thornburg

[57] ABSTRACT

An apparatus for laser surgery, particularly of the cornea is provided. Through this apparatus, a laser, especially a UV-laser, can be imaged on the tissue undergoing the operation. A diaphragm is arranged in the optical path of the laser and defines the illuminated region of the tissue. The diaphragm includes a slit which has a fixed angular alignment and an adjustable length and width. Further, an optical rotary device is provided which rotates the beam about an optical axis in between the slit and the tissue undergoing the operation.

7 Claims, 1 Drawing Sheet

APPARATUS FOR LASER SURGERY AND PARTICULARLY FOR THE KERATOTOMY OF THE CORNEA (III)

This is a continuation, of application Ser. No. 07/213,460, filed Jun. 29, 1988, now abandoned which is a continuation of application Ser. No. 07/030,830 filed as PCT DE86/00268 on Jun. 30, 1986, published as WO87/00038 on Jan. 15, 1987, now abandoned.

BACKGROUND AND SUMMARY OF THE INVENTION

The invention relates to an apparatus for laser surgery and particularly to keratotomy of the cornea using a laser, particuarly a UV-laser.

It is known, e.g. form the article "Excimer-Laser Surgery of the Cornea" by Stephen L. Trokel, American Journal of Ophthalmology, 1983, vol. 96, pp. 710–715 that in particular, argon-fluoride-excimer lasers with a wavelength of 193 nm are suitable for performing operations on the cornea. The object of such operations is e.g. to eliminate abnormal cornea curvatures by applying a specific "incison pattern". The literature discloses lasers of other wavelengths, e.g. r.f. lasers, which are suitable for keratotomy.

It is also known from the scientific literature, that light of other wavelengths is also suitable for keratotomy of the cornea.

In the known apparatuses for the keratotomy of the cornea, such as are e.g. described in the above article, a mask is placed just in front of the eye undergoinging the operation and is irradiated with UV-laser light.

As a result of this construction, the known apparatuses suffer from a number of disadvantages.

The laser beam must illuminate the diaphragm in which is located the desired "incision pattern" in a flat manner. As the incision pattern only takes up a small part of the illuminated surface, only a small part of the laser power is actually available for the operation.

An object of the present invention is to provide an apparatus for laser surgery and particularly for operating on the cornea, in which a large part of the laser power is available for the operation.

This object is achieved by providing the following apparatus. According to this invention, in place of the mask in which is provided the complete desired incision pattern, a single slit is used, whose alignment with respect to the laser beam remains unchanged throughout the operation and which is only modified with respect to its length and width. Following is provided the slit is provided an optical rotary device, is provided which rotates the slit image position on the tissue, e.g. the cornea on which the operation is to take place. As the laser beam now only has to illuminate the slit, whose angular alignment remains unchanged and in which only the length and width change within certain limits, substantially the complete laser power is available for the operation. Admittedly in the case of a complicated incision pattern, the individual parts thereof, e.g. in the case of a star-shaped incision pattern the individual arms of the star have to be successively illuminated, but as for each illumination process, a larger beam power is available, and the operating time is shorter than with the known apparatus, in which the complete incision pattern has to be illuminated with high absorbtion and/or reflection losses in the diaphragm.

In an advantageous feature of other preferred embodiments of the invention, the optical rotary device can be a known rotary prism, such as a Dove prism or an Oxley prism. However, in a preferred embodiment of the invention it is particularly advantageous to use a rotary prism formed from two parts whose entrance face and exit face are at right angles to the optical axis and that includes three surfaces, which totally reflect the beam and whose surface normals form an angle of 67.5°, 90°, and 112.5° with the optical axis. Further the prism includes two passage faces between the two parts through which the beam passes at right angles. In this embodiment of the prism, all the beam passage faces are at right angles to the optical path and the slit image is not interrupted by interfaces, boundary surfaces and the like.

Since particularly when operating on the cornea, the tissue undergoing the operation is not planar and is instead typically highly curved, it is particularly advantageous to use the inventive rotary device in conjunction with an optical device, which images the slit image with a high depth of field on the tissue undergoing the operation.

In an advantageous feature of other embodiments of the invention, it has suprisingly been found that such a device can be a simple telecentric arrangement of two positive optical elements between which is arranged the slit and which is to be projected on to the tissue undergoing the operation. The optical rotary device can also be arranged between two collecting optical elements, which form a telecentric arrangement, or alternatively can follow these two elements. The arrangement between the two positive optical elements has the advantage that a short, compact construction is obtained.

The inventive apparatus of all embodiments of the invention can at any time be integrated into an ophthalmic examination apparatus, such as an ophthalmoscope or a slit lamp device. In the case of integration into a slit lamp device, fitting can e.g. take place into the actual slit lamp, or into the microscope bracket, if the laser beam is to be projected by the microscope bracket on to the eye. Such an apparatus has been proposed for a neodymium-YAG laser, whilst apparatuses in which the reflecting takes place by slit lamps have already been proposed for argon lasers. This known beam guidance can also be used for apparatuses with excimer lasers or lasers of other wavelengths, such as r.f. lasers and in other embodiments of the invention it is particularly advantageous to construct all the deflectors as fused quartz prisms, because in the case thereof the reflection losses are much lower than in the case of coated reflecting surfaces.

It is also possible to integrate all embodiments of the invention, into an apparatus, such as is described in a commonly-owned patent application filed on the same date filed Jun. 29, 1985 in Germany, Pat. No. 35 23 342.7. In this apparatus, the slit lamp is not privoted and is instead merely linearly displaced, whilst the chin rest is also movable. In this apparatus, the number of reflecting surfaces required for reflecting in the laser beam is particularly small, so that a particularly large proportion of the laser power is available for the operation. The reduction of the number of mirros used for guiding the beam compensates for any losses due to the rotary prisms.

The inventive apparatus has the advantage that a much larger proportion of the laser power is available for the actual operation than was the case in the known apparatuses. The inventively provided illumination of a slit fixed with respect to its alignment is assisted by the fact that an excimer laser without beam-forming measures already has an elongated cross-section, so that a beam section shape, when illuminates the slit in a coinciding manner can be achieved with simple measures, e.g. with a telecentric arrangement or with cylindrical lenses. Other objects, advantages and novel features of the present invention will become apparent from the following detailed description of the invention when considered in conjunction with the accompanying drawing.

DETAILED DESCRIPTION OF THE DRAWINGS

Figure 1:
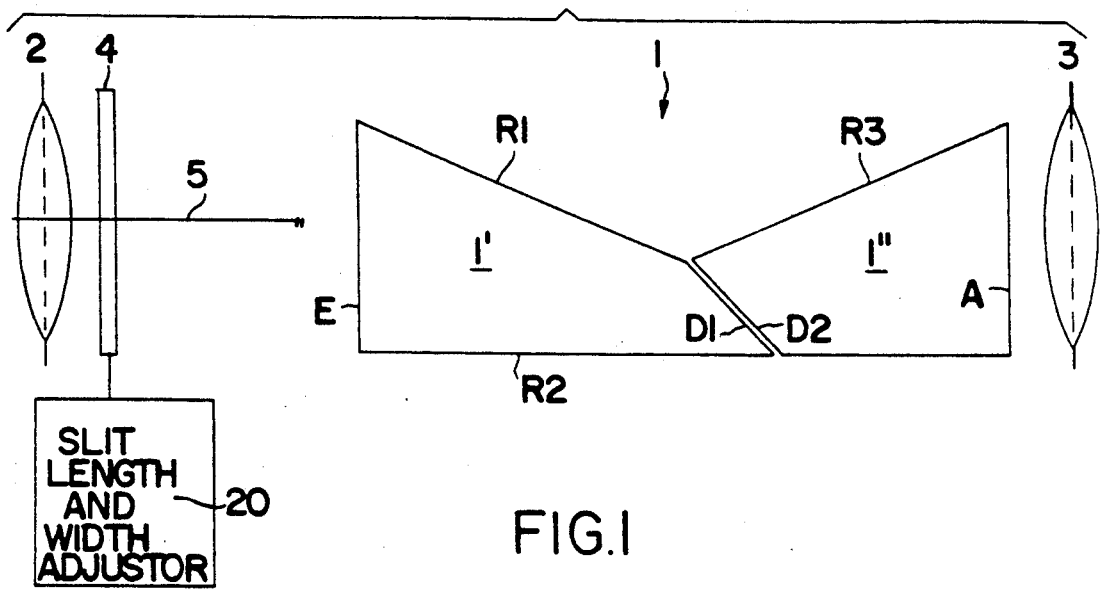
FIG. 1 is a cross-section view through an embodiment of the invention.
Figure 2:
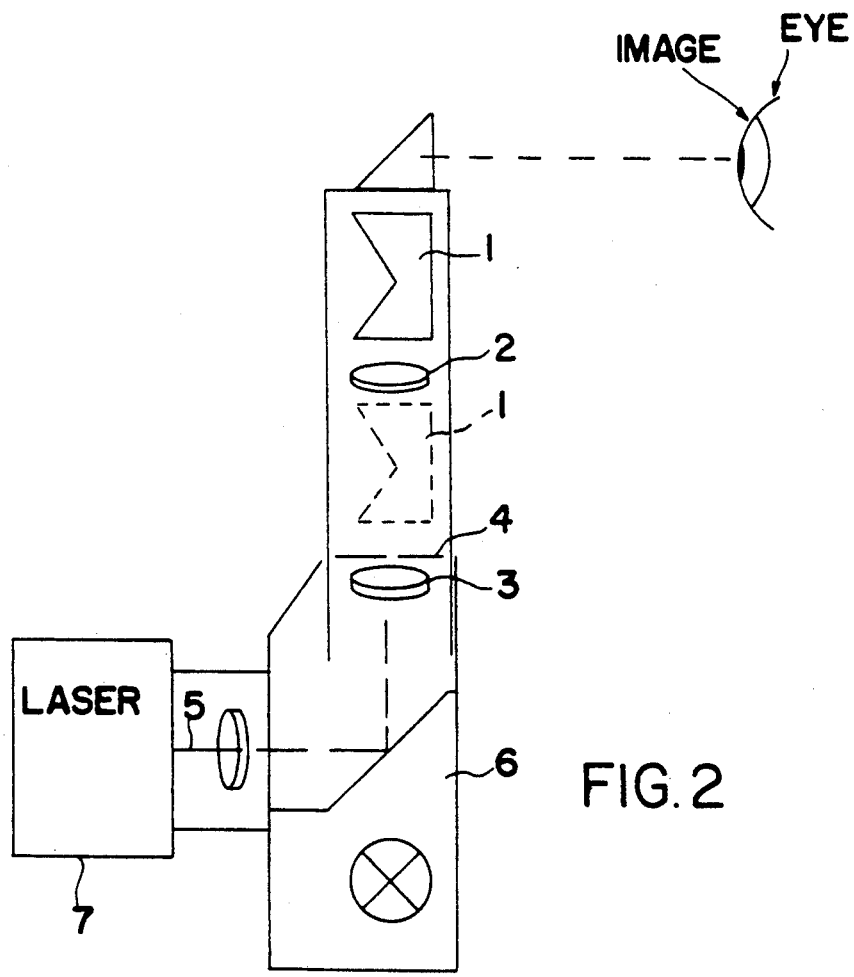
FIG. 2 is a longitudinal sectional view illustrating an embodiment of the rotary optical prism of the present invention relative to a slit lamp and an ultraviolet laser arrangement.

FIG. 1 shows a rotary prism in dashed lines, 1, which is positioned between two optical elements 2, 3 with a positive power. Between optical element 2 and rotary prism 1 is provided a slit 4, whose angular alignment remains unchanged with respect to the laser beam 5 of a excimer laser 7 as shown in FIG. 2 and whose length and width are adjustable in accordance with the particular requirements by adjusting mechanism 20.

Lenses 2 and 3 form a telecentric arrangement, i.e. the sum of their focal length is the same as their optical spacing. As a result of the telecentric arrangement of the two positive optical elements 2, 3, it is achieved in conjunction with the coherence of laser beam 5, that slit 4 is imaged with a high depth of field on to the tissue undergoing the operation. For example, in the case of a focal length of optical element 2 of approximately 200 mm and a focal length of optical element 3 of approximately 50 to 100 mm, a depth of field of several millimeters is obtained, so that the slit image is imaged in an acute manner, even on the most curved part of the cornea.

It is expressly pointed out that this high depth of field is obtained through the coherence of the laser light in conjunction with the telecentric arrangement of the two positive optical elements 2, 3. On illuminating the slit with incoherent light, e.g. the light of a slit lamp, even when orienting the slit image, it is not possible to obtain an image formation with such a high depth of field as when illuminating with coherent light.

The optical rotary device 1 as best seen in FIG. 1 comprises two parts 1' and 1''. Part 1' has an entrance face E at right angles to laser beam 5, reflecting faces R1 and R2, as well as a beam passage face D1, through which the beam passes over into part 1'' of the prism. Reflecting face R1 is inclined by an angle of 22.5°, in the direction which can be gathered from the drawing, with respect to the laser beam 5 in front of the prism, i.e. to the optical axis, whilst reflecting face R2 is parallel to the optical axis. Passage face D1 forms an angle of 45° with the optical axis in the direction which can be gathered from the drawing.

Part 1'' of the rotary prism has a beam entrance face D2, a reflecting face R3 and a beam exit face A, which is at right angles to the optical axis. The beam entrance face D2 is parallel to face D1, whilst reflecting face R3 has an angle of 22.5° to the optical axis 5, in the direction which can be gathered from the drawing.

Between the two faces D1, D2 is provided an air gap. Alternatively the two faces are optically contacted, but are not cemented.

The present prism has a number of advantages. Compared with known Oxley prisms, the reflecting face R2 is not interrupted by a cemented surface or the like, so that there are no disturbances in the slit image. Nevertheless, the prism proposed by the invention is easy to manufacture.

The apparatus according to the invention has been described in exemplified manner hereinbefore. Within the scope of the inventive concept of using a slit with a fixed alignment or orientation, whose image is rotated on the tissue undergoing the operation by means of an optical rotary device, the most varied modifications are possible.

Naturally the optical rotary device can also be used without a projection device, which gives a high depth of field of the slit image, in cases where there is not interest in a high acuity, or if the tissue undergoing the operation is not extremely curved.

When using the above-described projection device for high depth of field and which comprises two collecting optical elements, the optical rotary device can also be positioned after the second collecting element 2, as shown in solid lines in FIG. 2.

The drawing diagrammatically shows the optical elements 2 and 3 as simple lenses. However, naturally these optical elements could also comprise several lenses and optically be designed in such a way that they so influence the beam section of the laser beam, that it illuminates in "coinciding" manner the slit, without greater edge losses.

In addition, special measures can be taken which so expand the already oval cross-section of an excimer laser in such a way that the losses through the slit edge region are as small as possible.

In particular, it is possible to additionally provide a sighting and alignment device, which projects through the invention apparatus the light in the visible range along the same light path as the UV-laser, so that the position of the slit image on the tissue undergoing the operation can be optically checked, as shown in FIG. 2. This optical sighting device can e.g. be realized in that the inventive apparatus is incorporated into a slit lamp 6 as shown in FIG. 2. It is naturally also possible to provide a second laser, e.g. a helium-neon laser, which functions in the visible range.

The optical elements 2 and 3 should then be constructed as UV-achromates and can e.g. be formed from $CaF_2$ and $SiO_2$.

It is in particular possible to integrate the inventive apparatus, which is based on the basic idea of using the already oval beam of a UV-excimer laser for illuminating a slit which is fixed with respect to it angular alignment and to optically rotate the slit image on the tissue undergoing the operation into random optical and in particular ophthalmic examination equipment, such as ophthalmoscopes, slit lamp devices and the like.

It is naturally also possible to use other lasers, e.g. r.f. lasers with a wavelength of approximately 3 $\mu$m.

Although the present invention has been described and illustrated in detail, it is to be clearly understood that the same is by way of illustration and example only, and is not to be taken by way of limitation. The spirit and scope of the present invention are to be limited only by the terms of the appended claims.

We claim:

1. Eye surgery apparatus for controlling the application of a laser beam on tissue of a cornea to perform keratotomy of the cornea, said apparatus comprising:

a slit diaphragm disposable between a laser beam source and a cornea to be operated on, said slit diaphragm including a control slit through which the laser beam passage along an optical device during surgery, and optical rotary means diposed between the slit diaphragm and the cornea for accommodating controlled movement of the laser beam impact position on the cornea, whereby optimum laser beam power can be directed at the diaphragm control slit during surgical operation; and wherein the optical rotary means includes a prism formed from two parts, said prism including an entrance face and an exit face, said entrance face and exit face being at right angles to the optical axis, three reflecting surfaces totally reflecting the beam and having normals forming an angle of 67.5°, 90°, and 125.5° with the optional axis respectively, and two passage faces between the two parts through which the laser beam passes at right angles.

2. Eye surgery apparatus according to claim 1, wherein the control slit has a fixed angular alignment and an adjustable length and width.

3. Eye surgery apparatus according to claim 1, further including two collecting optical elements which form a telecentric arrangement, said control slit being arranged between said two collecting optical elements.

4. Eye surgery apparatus according to claim 3, wherein the optical rotary means is arranged between said two collecting optical elements.

5. Eye surgery apparatus according to claim 1, further including an image-forming means for aligning a visible slit image on the cornea.

6. Eye surgery apparatus according to claim 5, wherein the image-forming means includes a slit lamp, said slit lamp containing the control slit which simultaneously constitues the central slit for the laser beam and a visible light beam forming the visible slit image.

7. Eye surgery apparatus according to claim 6, wherein the control slit has a fixed angular alignment and an adjustable length and width.

* * * * *

UNITED STATES PATENT AND TRADEMARK OFFICE
CERTIFICATE OF CORRECTION

PATENT NO. : 5,000,751

DATED : March 19, 1991

INVENTOR(S) : Schröder et al

It is certified that error appears in the above-identified patent and that said Letters Patent is hereby corrected as shown below:

Col. 5, line 23 "125.5°" has been changed to "112.5°"

Col. 5, line 23 "optional" has been changed to "optical"

Signed and Sealed this

First Day of June, 1993

Attest:

Attesting Officer

MICHAEL K. KIRK

Acting Commissioner of Patents and Trademarks